(12) United States Patent
Mueller (10) Patent No.: US 8,968,356 B2
(45) Date of Patent: Mar. 3, 2015

(54) SURGICAL DEVICE AND HANDLE ASSEMBLY FOR USE THEREWITH

(71) Applicant: Covidien LP, Mansfield, MA (US)

(72) Inventor: Peter M. Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/801,379

(22) Filed: Mar. 13, 2013

(65) Prior Publication Data

US 2014/0039470 A1   Feb. 6, 2014

Related U.S. Application Data

(60) Provisional application No. 61/680,120, filed on Aug. 6, 2012.

(51) Int. Cl.
*A61B 17/00*   (2006.01)
*A61B 18/14*   (2006.01)
*A61B 17/29*   (2006.01)
*A61B 18/00*   (2006.01)
*A61B 19/00*   (2006.01)

(52) U.S. Cl.
CPC ............. *A61B 17/00* (2013.01); *A61B 18/1445* (2013.01); *A61B 2017/2927* (2013.01); *A61B 2017/2929* (2013.01); *A61B 2017/00323* (2013.01); *A61B 2017/00876* (2013.01); *A61B 2018/0063* (2013.01); *A61B 2019/301* (2013.01)
USPC ........................................................ 606/205

(58) Field of Classification Search
CPC .... A61B 17/28; A61B 17/2841; A61B 17/29; A61B 2017/2903

USPC ......... 606/51–52, 205–208; 16/430; 173/176; 81/342, 376

See application file for complete search history.

(56) References Cited

U.S. PATENT DOCUMENTS

| D249,549 S | 9/1978 | Pike |
| D279,075 S | 6/1985 | Nuesse et al. |
| D280,378 S | 9/1985 | Nuesse et al. |
| D298,353 S | 11/1988 | Manno |
| D299,413 S | 1/1989 | DeCarolis |
| D343,453 S | 1/1994 | Noda |

(Continued)

FOREIGN PATENT DOCUMENTS

| EP | 1201192 | 2/2006 |
| EP | 1785101 | 5/2007 |

(Continued)

OTHER PUBLICATIONS

U.S. Appl. No. 13/847,350, filed Mar. 19, 2013; Mueller.

*Primary Examiner* — Todd Manahan
*Assistant Examiner* — Erich Herbermann (57) ABSTRACT

A surgical instrument is disclosed. A rotation mechanism is disposed in mechanical cooperation with a handle assembly and effects rotation of an end effector. The rotation mechanism includes a first member including at least one magnet, and a second member including at least one magnet. The first member and the second member define a space therebetween. The articulation mechanism is disposed in mechanical cooperation with the handle assembly and effects articulation of the end effector. The articulation mechanism includes a plurality of tendons. Each tendon extends longitudinally through the space between the first member and the second member of the rotation mechanism.

10 Claims, 9 Drawing Sheets

(56) References Cited

U.S. PATENT DOCUMENTS

| | | | |
|---|---|---|---|
| D358,887 S | 5/1995 | Feinberg | |
| D394,994 S | 6/1998 | Dreve | |
| 5,800,499 A * | 9/1998 | Ollivier | 607/126 |
| D402,028 S | 12/1998 | Grimm et al. | |
| D453,376 S | 2/2002 | McMahon et al. | |
| 6,517,560 B1 | 2/2003 | Toth et al. | |
| 6,592,581 B2 | 7/2003 | Bowe | |
| 6,605,086 B2 | 8/2003 | Hayzelden et al. | |
| 6,648,875 B2 | 11/2003 | Simpson et al. | |
| 6,652,517 B1 | 11/2003 | Hall et al. | |
| D495,413 S | 8/2004 | Perry et al. | |
| D496,997 S | 10/2004 | Dycus et al. | |
| D499,181 S | 11/2004 | Dycus et al. | |
| D524,625 S | 7/2006 | Wu | |
| D527,600 S | 9/2006 | Stratford | |
| D531,311 S | 10/2006 | Guerra et al. | |
| D531,872 S | 11/2006 | Aglassinger | |
| D533,274 S | 12/2006 | Visconti et al. | |
| D541,418 S | 4/2007 | Schechter et al. | |
| D541,611 S | 5/2007 | Aglassinger | |
| D547,154 S | 7/2007 | Lee | |
| D550,052 S | 9/2007 | Lee | |
| D559,386 S | 1/2008 | Pease et al. | |
| D575,401 S | 8/2008 | Hixson et al. | |
| D582,038 S | 12/2008 | Swoyer et al. | |
| D582,742 S | 12/2008 | Aglassinger | |
| 7,594,903 B2 | 9/2009 | Webler et al. | |
| D605,488 S | 12/2009 | Aglassinger | |
| D605,489 S | 12/2009 | Aglassinger | |
| D627,066 S | 11/2010 | Romero | |
| D628,289 S | 11/2010 | Romero | |
| D628,290 S | 11/2010 | Romero | |
| 7,998,112 B2 | 8/2011 | Chow et al. | |
| 2006/0020287 A1 * | 1/2006 | Lee et al. | 606/205 |
| 2007/0261868 A1 * | 11/2007 | Gross | 173/2 |
| 2009/0171147 A1 * | 7/2009 | Lee et al. | 600/104 |
| 2009/0299344 A1 * | 12/2009 | Lee et al. | 606/1 |
| 2011/0184405 A1 * | 7/2011 | Mueller | 606/41 |

FOREIGN PATENT DOCUMENTS

| | | |
|---|---|---|
| EP | 1842500 | 10/2007 |
| JP | 2001-276091 A | 10/2001 |
| WO | 95/07662 | 3/1995 |
| WO | 2006/135964 A1 | 12/2006 |
| WO | 2008/045348 A2 | 4/2008 |
| WO | 2008/045350 A2 | 4/2008 |
| WO | 2009/039510 A1 | 3/2009 |
| WO | 2011/005335 A1 | 1/2011 |

* cited by examiner

SURGICAL DEVICE AND HANDLE ASSEMBLY FOR USE THEREWITH

CROSS REFERENCE TO RELATED APPLICATION

The present application claims the benefit of and priority to U.S. Provisional Application Ser. No. 61/680,120, filed on Aug. 6, 2012, the entire contents of which are incorporated herein by reference.

BACKGROUND

The present disclosure relates to a device for surgically manipulating tissue. More particularly, the present disclosure relates to a device for surgically joining and/or cutting tissue utilizing an elongated shaft and a handle assembly.

Technical Field

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

Another example of a surgical instrument used to surgically join tissue is an electrosurgical forceps, which utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

SUMMARY

One aspect of the present disclosure relates to a surgical instrument including a handle assembly, an elongated shaft, an end effector, a rotation mechanism and an articulation mechanism. The elongated shaft extends distally from the handle assembly and defines a first longitudinal axis. The end effector is disposed in mechanical cooperation with a distal portion of the elongated shaft and defines a second longitudinal axis. The rotation mechanism is disposed in mechanical cooperation with the handle assembly and effects rotation of the end effector about the second longitudinal axis. The rotation mechanism includes a first member including one or more magnets disposed in mechanical cooperation therewith, and a second member including one or more magnets disposed in mechanical cooperation therewith. The first member and the second member define a space therebetween. The articulation mechanism is disposed in mechanical cooperation with the handle assembly and effects movement of the end effector from a first position where the first longitudinal axis is substantially aligned with the second longitudinal axis to a second position where the second longitudinal axis is displaced from the first longitudinal axis. The articulation mechanism includes a plurality of tendons. Each tendon extends longitudinally through the space between the first member and the second member of the rotation mechanism.

In disclosed embodiments, the surgical instrument includes a tip catheter disposed in mechanical cooperation with the first member of the rotation mechanism. The tip catheter is substantially parallel with each tendon along at least a majority of entire length of the tip catheter.

In another aspect of the present disclosure, the first member of the rotation mechanism includes four magnets thereon, and the second member includes four magnets thereon. Each of the four magnets of the first member is substantially equally spaced around an outer perimeter of the first member. Each of the four magnets of the second member is substantially equally spaced around an inner perimeter of the second member.

In disclosed embodiments, the first and second members are ring-shaped defining an annular space therebetween. The first and/or second member may be configured to form a closed ring. The first member and the second member may be positioned in substantially the same longitudinal position relative to one another or co-axially disposed relative to one another.

In disclosed embodiments, the handle assembly includes a movable handle that is configured to be engaged by a user. The movable handle is movable between a first position where jaw members of the end effector are in an open position and a second position where the jaw members are in an approximated position. The movable handle is disposed substantially parallel to the first longitudinal axis when the movable handle is in one of the first position, the second position or any position therebetween.

In other aspects of the present disclosure, a surgical instrument is disclosed which included a handle assembly, an elongated shaft, an end effector, and an actuation rod. The handle assembly includes a housing and a movable handle that is configured to be engaged by a user. The elongated shaft extends distally from the handle assembly and defines a first longitudinal axis. The end effector is disposed in mechanical cooperation with a distal portion of the elongated shaft and defines a second longitudinal axis. The end effector includes jaw members that are movable between an open position and an approximated position. The actuation rod is disposed in mechanical cooperation with the handle assembly and with the end effector. The actuation rod is configured for longitudinal translation with respect to the handle portion. The movable handle is movable between a first position where the jaw members of the end effector are in an open position and a second position where the jaw members are in an approximated position. The movable handle is disposed substantially parallel to the first longitudinal axis when the movable handle is in one of the first position, the second position and any position therebetween. A proximal portion of the movable handle is pivotally attached to a proximal portion of a proximal link. A distal portion of the proximal link is pivotally attached to a proximal portion of a distal link via a pin. The pin is movable towards and away from the longitudinal axis. A distal portion of the distal link is pivotably connected to the housing.

In embodiments, the movable handle is pivotable about a fulcrum that is disposed between the proximal portion of the movable handle and a distal portion of the movable handle.

Pivoting the proximal portion of the movable handle causes the actuation rod to move in a first longitudinal direction. Pivoting the distal portion of the movable handle causes the actuation rod to move in a second longitudinal direction. The first longitudinal direction being opposite from the second longitudinal direction. The fulcrum may be disposed substantially in the longitudinal center of the movable handle. The distal portion of distal link may be disposed in fixed alignment with the longitudinal axis.

In other aspects of the present disclosure, a rotation mechanism is included with the rotation assembly and is disposed in mechanical cooperation with the handle assembly for effecting rotation of the end effector about the second longitudinal axis. The rotation mechanism includes a first member including one or more magnets disposed in mechanical cooperation therewith, and a second member including one or more magnets disposed in mechanical cooperation therewith. The first member and the second member define a space therebetween. In other aspects, the surgical instrument may include an articulation mechanism disposed in mechanical cooperation with the handle assembly for effecting movement of the end effector from a first position where the first longitudinal axis is substantially aligned with the second longitudinal axis to a second position where the second longitudinal axis is displaced from the first longitudinal axis. The articulation mechanism may include a plurality of tendons each extending longitudinally through the space between the first member and the second member of the rotation mechanism.

In embodiments, a portion of the proximal link is disposed in mechanical cooperation with the actuation rod.

BRIEF DESCRIPTION OF THE DRAWINGS

Various embodiments of the presently disclosed surgical instrument are described herein with reference to the drawings wherein.

DETAILED DESCRIPTION

Figure 1:
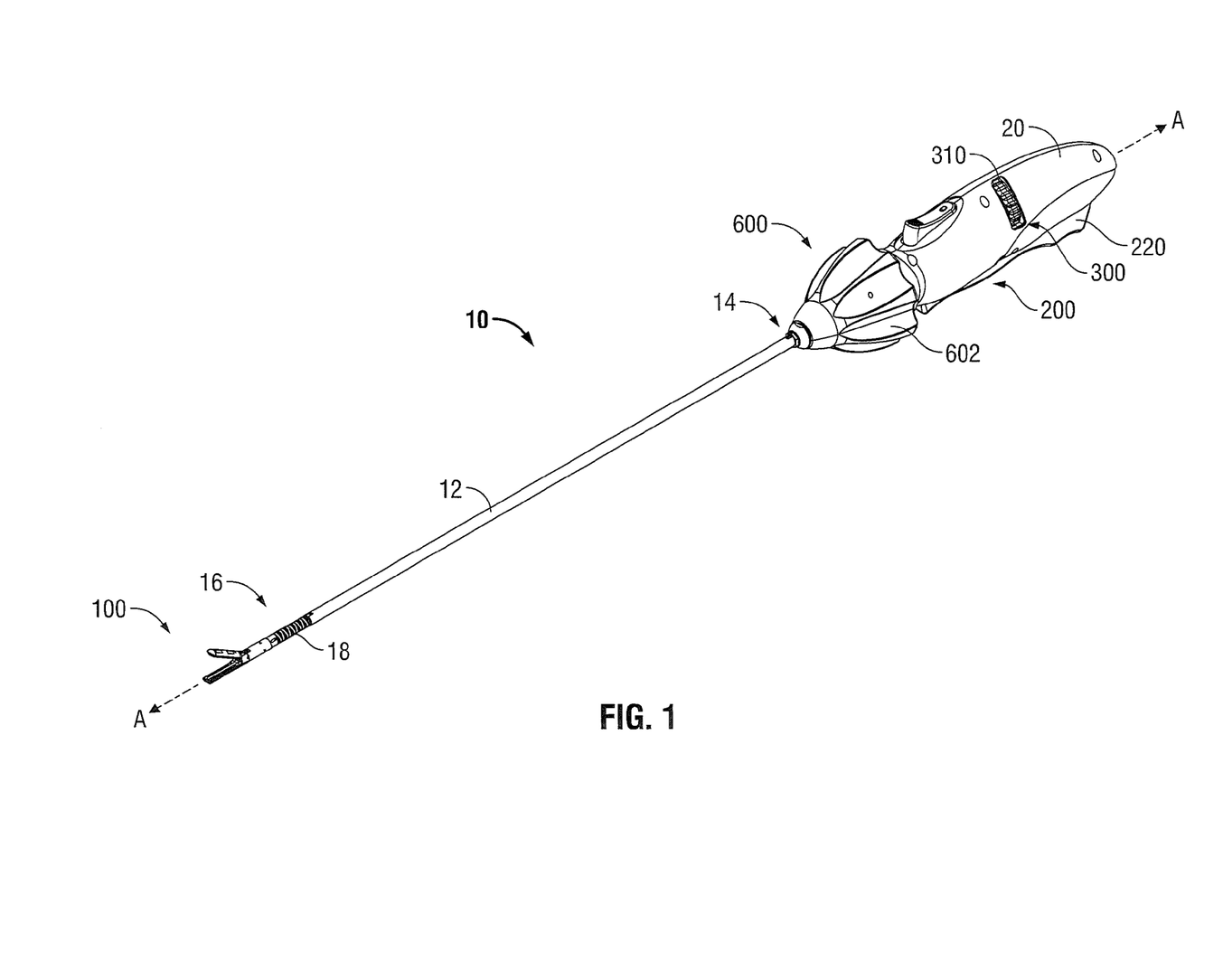
FIG. 1 is a perspective view of an endoscopic forceps in accordance with the present disclosure illustrating the jaw members of the end effector in an open position.

Referring initially to FIG. 1, one embodiment of an endoscopic vessel sealing forceps is depicted generally as 10. In the drawings and in the descriptions which follow, the term "proximal," as is traditional, will refer to the end of the forceps 10 which is closer to the user, while the term "distal" will refer to the end which is farther from the user. The forceps 10 comprises a housing 20, an end effector assembly 100 and an elongated shaft 12 extending therebetween to define a first longitudinal axis A-A. A handle assembly 200, an articulation assembly 300, and a rotation assembly 600 are operable to control the end effector assembly 100 to grasp, seal and/or divide tubular vessels and vascular tissue. Although the forceps 10 is configured for use in connection with bipolar surgical procedures, various aspects of the present disclosure may also be employed for monopolar surgical procedures. Additionally, while the figures depict a certain type of a forceps, other types of forceps and other endoscopic surgical instruments are encompassed by the present disclosure. Further details of endoscopic forceps are described in commonly-owned U.S. Patent Publication No. 2010/0179540 to Marczyk et al., and U.S. patent application Ser. No. 12/718, 143 to Marczyk et al., the entire contents of each of which are hereby incorporated by reference herein Further details of an endoscopic surgical stapling instrument including surgical fasteners are described in commonly-owned U.S. Pat. No. 6,953,139 to Milliman et al., the entire contents of which are hereby incorporated by reference herein.

Generally, handle assembly 200 includes a movable handle 220 that is movable with respect to housing 20 to induce relative movement between a pair of jaw members of the end effector assembly 100. The movable handle 220 is operatively coupled to the end effector assembly 100 via a drive rod, actuation rod, tip catheter or a flexible drive rod 50 (FIGS. 2 and 5-8), which extends through the elongated shaft 12, and longitudinally reciprocates to induce movement of at least one jaw member. The movable handle 220 is movable with respect to housing 20 to move the jaw members from an open position wherein the jaw members are disposed in spaced relation relative to one another, to a clamping or approximated position wherein the jaw members cooperate to grasp tissue therebetween. Electrosurgical energy may be transmitted through tissue grasped between jaw members to effect a tissue seal. Further details of these components and various other components of the disclosed forceps are disclosed in the references that have incorporated above.

Elongated shaft 12 of forceps 10 includes a distal portion 16 configured to mechanically engage the end effector assembly 100 and a proximal portion 14, which mechanically engages the housing 20. The distal portion 16 of shaft 12 is shown including an exterior casing or insulating material disposed over a plurality of links 18. The links 18 are configured to pivot relative to one another to permit the end effector 100, which defines a second longitudinal axis B-B, to articulate relative to the first longitudinal axis A-A. The links 18 may be shaped to permit the distal portion 16 of the shaft 12 to be self-centering, or to have a tendency to return to an unarticulated configuration.

Articulation assembly 300 sits on housing 20 and is operable via an articulation control 310 (and/or a second articulation control, which is not explicitly illustrated in the accompanying figures) to move the end effector assembly 100 (and the articulating distal portion 16 of the shaft 12) in the direction of arrows "R, L" relative to the first longitudinal axis A-A. The links 18 each include a central lumen extending longitudinally therethrough. The central lumen permits passage of various actuators, including a drive rod, a knife rod and four tendons, or steering cables 901, 902, 903 and 904 (e.g., FIG. 2) through the elongated shaft 12.

The four steering cables 901-904 may be substantially elastic and slideably extend through elongated shaft 12. A distal end of the each of the steering cables 901-904 is mechanically engaged with the end effector 100. Proximal ends of the steering cables 901-904 are operatively coupled to the articulation control 310 as described below. Further, while a single articulation control 310, and four cables 901-904 are illustrated, it is envisioned and within the scope of the present disclosure the forceps 10 includes more than one articulation control, and more or fewer than four cables (e.g., two cables). For example, forceps 10 may include one articulation control and two cables, forceps 10 may include two articulation controls and four cables, e.g., two cables operatively coupled to each articulation control, and forceps may include one articulation control and four cables. Further details on an articulation mechanism are disclosed in U.S. Patent Application Ser. No. 61/505,604 to Marczyk, et al, filed on Jul. 8, 2011, the entire contents of which being incorporated by reference herein.

Figure 2:
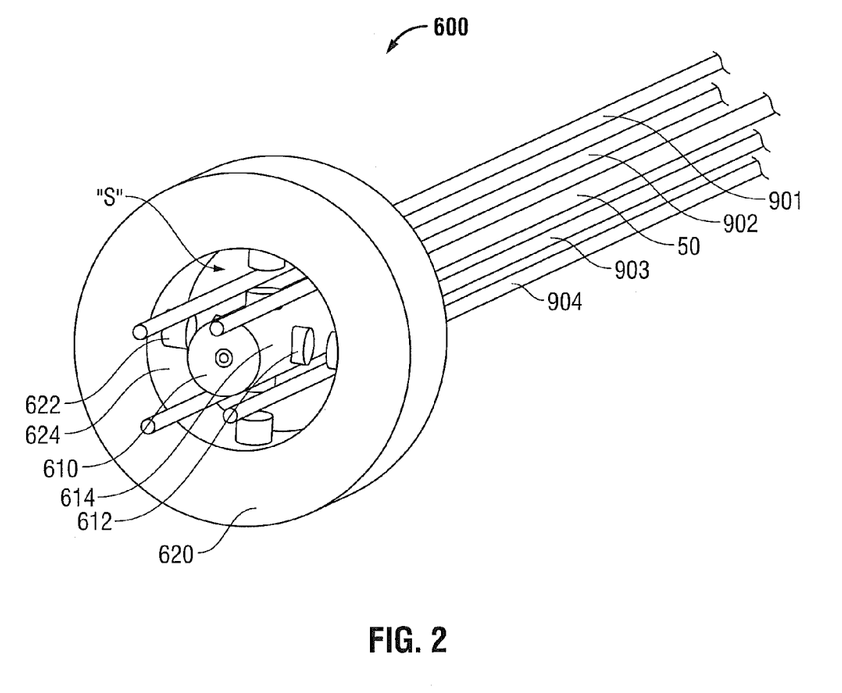
FIG. 2 is a perspective view of a rotation assembly of the present disclosure.
Figure 3:
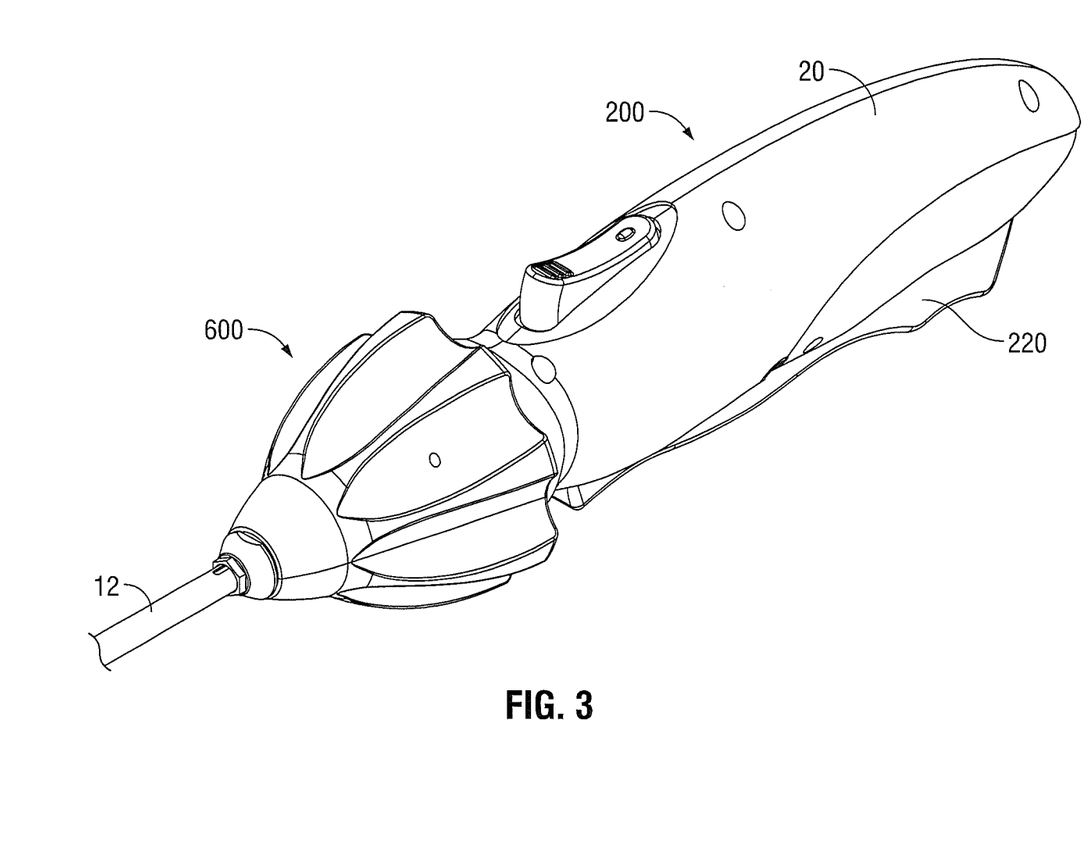
FIGS. 3 and 4 are perspective view of the handle assembly of the present disclosure.
Figure 4:
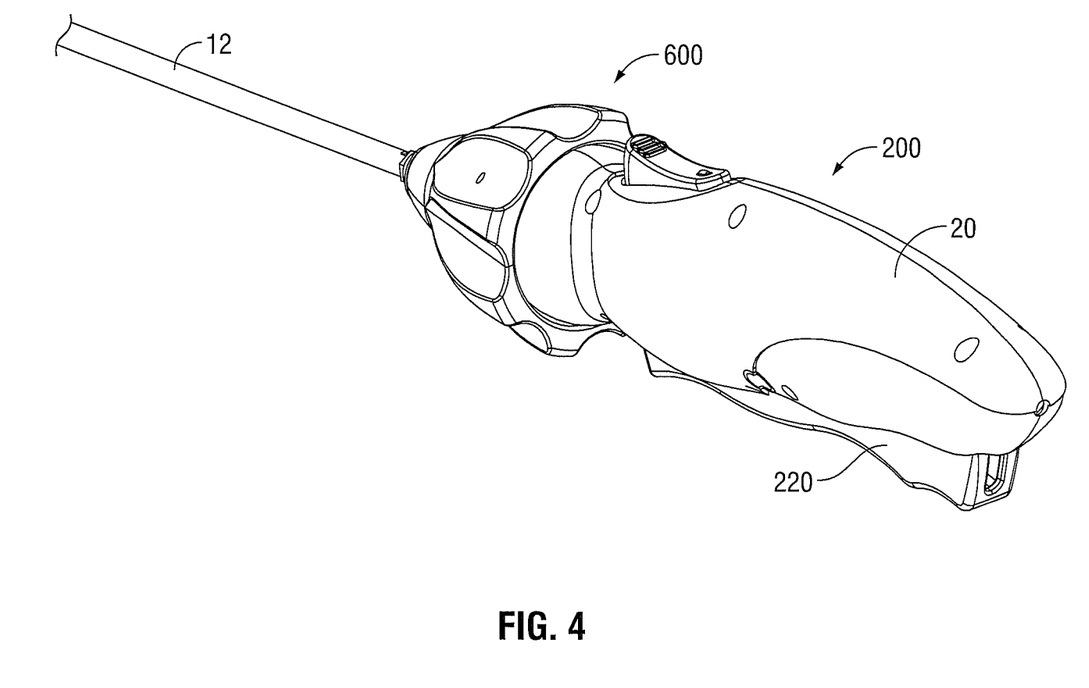

An embodiment of the disclosed rotation assembly 600 is illustrated in FIG. 2. Rotation assembly 600 includes a first member 610, and a second member 620. First member 610 is ring-like and includes a plurality of magnets 612 around its outer perimeter 614. For example, four magnets 612 are substantially equally spaced around the outer perimeter 614. Additionally, first member 610 is mechanically coupled to the tip catheter 50. Second member 620 is also ring-like and includes a plurality of magnets 622 around its inner perimeter 624. For example, four magnets 622 are substantially equally spaced around the inner perimeter 624. All of the magnets 612 on the first member 610 may have a first polarity, and all of the magnets 622 of the second member 620 may have a second, opposite polarity, thus creating magnetic attraction fields between the two members 610, 620.

Figure 1A:
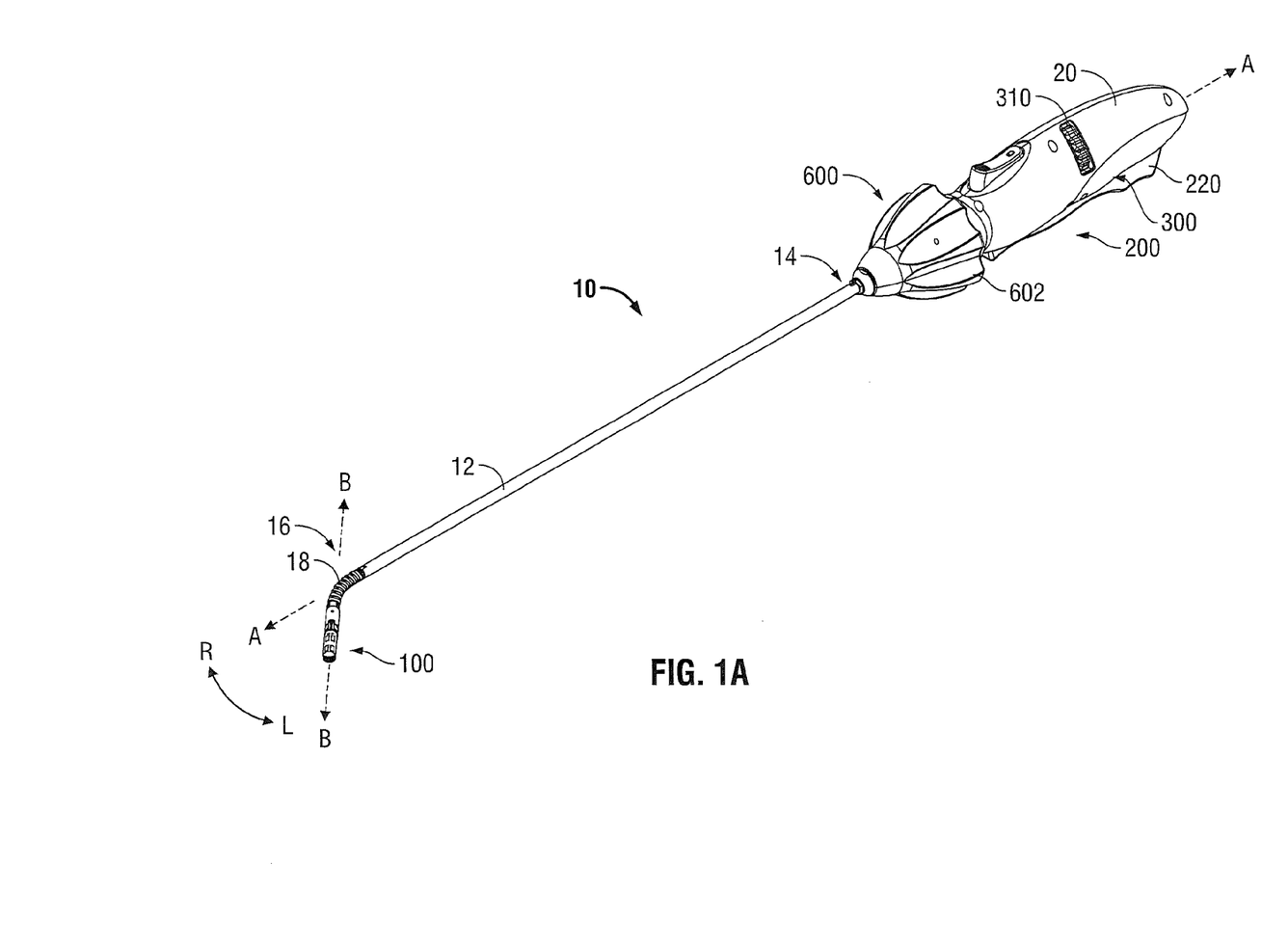
FIG. 1A is a perspective view of the endoscopic forceps of FIG. 1 illustrating the jaw members in an approximated position, and the end effector in an articulated position.

The second member 620 is also mechanically coupled to a user-accessible rotation wheel 602 (see FIGS. 1 and 1A, for example), such that rotation of rotation wheel 602 results in rotation of second member 620. Additionally, due to the magnetic attraction between the first member 610 and the second member 620, as discussed above, rotation of the second member 620 provides torque to the first member 610, which causes the first member 610 to rotate (e.g., the same or a corresponding amount of rotation). Further, rotation of the first member 610 causes the tip catheter 50 to rotate (e.g., the same or a corresponding amount of rotation), since, as discussed above, the first member 610 is mechanically coupled to the tip catheter 50. Therefore, when a user rotates rotation wheel 602, the second member 620, the first member 610, the tip catheter 50, and the end effector assembly 100, which is mechanically coupled to the tip catheter 50, each rotate (e.g., the same or a corresponding amount of rotation). That is, despite the lack of a mechanical connection between the first member 610 and the second member 620, rotation of the rotation wheel 602 causes the end effector assembly 100 to rotate. Additionally, the magnetic engagement between first member 610 and second member 620 acts as a safety clutch, which allows a limited amount of torque transmission to tissue. Further, it is envisioned that magnets 612 and 622 include a "spring rate" and will allow or facilitate breakaway, cogging, and resetting.

With continued reference to FIG. 2, the first member 610 and the second member 620 of the rotation assembly 600 are longitudinally aligned and are disposed coaxially. Additionally, an annular space "S" is defined between the first member 610 and the second member 620. As shown, the steering cables 901, 902, 903 and 904 extend longitudinally through the annular space "S." Thus, since there is no physical mechanical link (e.g., no spokes) between the first member 610 and the second member 620, the location of the steering cables 901, 902, 903 and 904 though the annular spaced "S" does not interfere with the rotation of the first member 610 and/or the second member 620. Moreover, the annular space "S" allows a full 360° rotation, for example, of the first member 610 and the second member 620 without effecting the position of the steering cables 901, 902, 903 and 904.

While each of the first member 610 and the second member 620 are shown and described having four magnets 612, 622, respectively, it is within the scope of the present disclosure that each member 610, 620 includes more or fewer than four magnets. Additionally, it is within the scope of the present disclosure that the first member 610 has more or fewer magnets 612 than the number of magnets 622 on the second member 620.

With reference to FIGS. 3-8, handle assembly 200 in accordance with embodiments of the present disclosure is shown. Handle assembly 200 includes housing 20, movable handle 220, a proximal link 230 and a distal link 240. Generally, movable handle 220 is pivotable with respect to the housing 20 about a first pivot 250. (Articulation assembly 300 is omitted from FIGS. 3-8 for clarity.)

Figure 6:
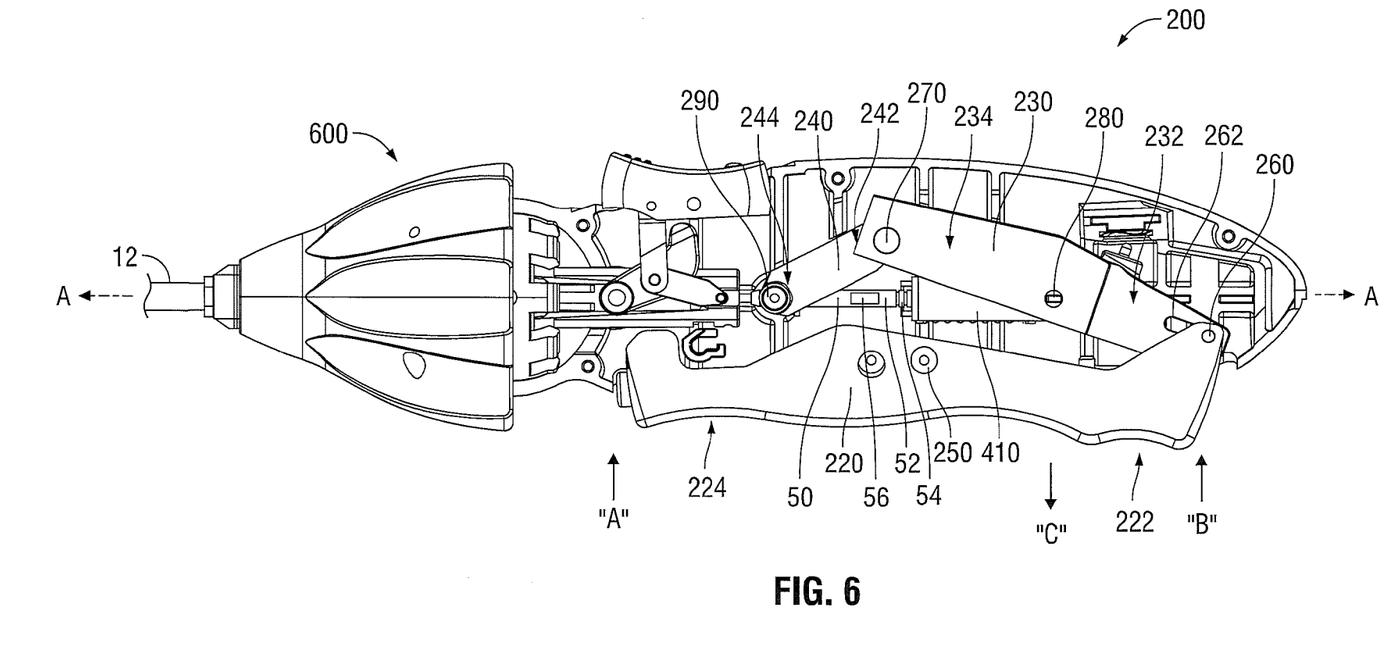
FIGS. 6-8 are partial longitudinal cross-sectional views of the handle assembly of the present disclosure in various stages of operation.

In use, actuation of a distal portion 224 of movable handle 220 in the general direction of arrow "A" in FIG. 6 (i.e., towards the longitudinal axis A-A), causes opening of the jaw members; actuation of the proximal portion 222 of movable handle 220 in the general direction of arrow "B" (i.e., towards the longitudinal axis A-A) causes approximation of the jaw members. More particularly, when a user actuates distal portion 224 of movable handle 220, movable handle 220 pivots about its fulcrum or first pivot 250, which causes proximal portion 222 to move in the general direction of arrow "C" in FIG. 6 (i.e., away from the longitudinal axis A-A).

Figure 5:
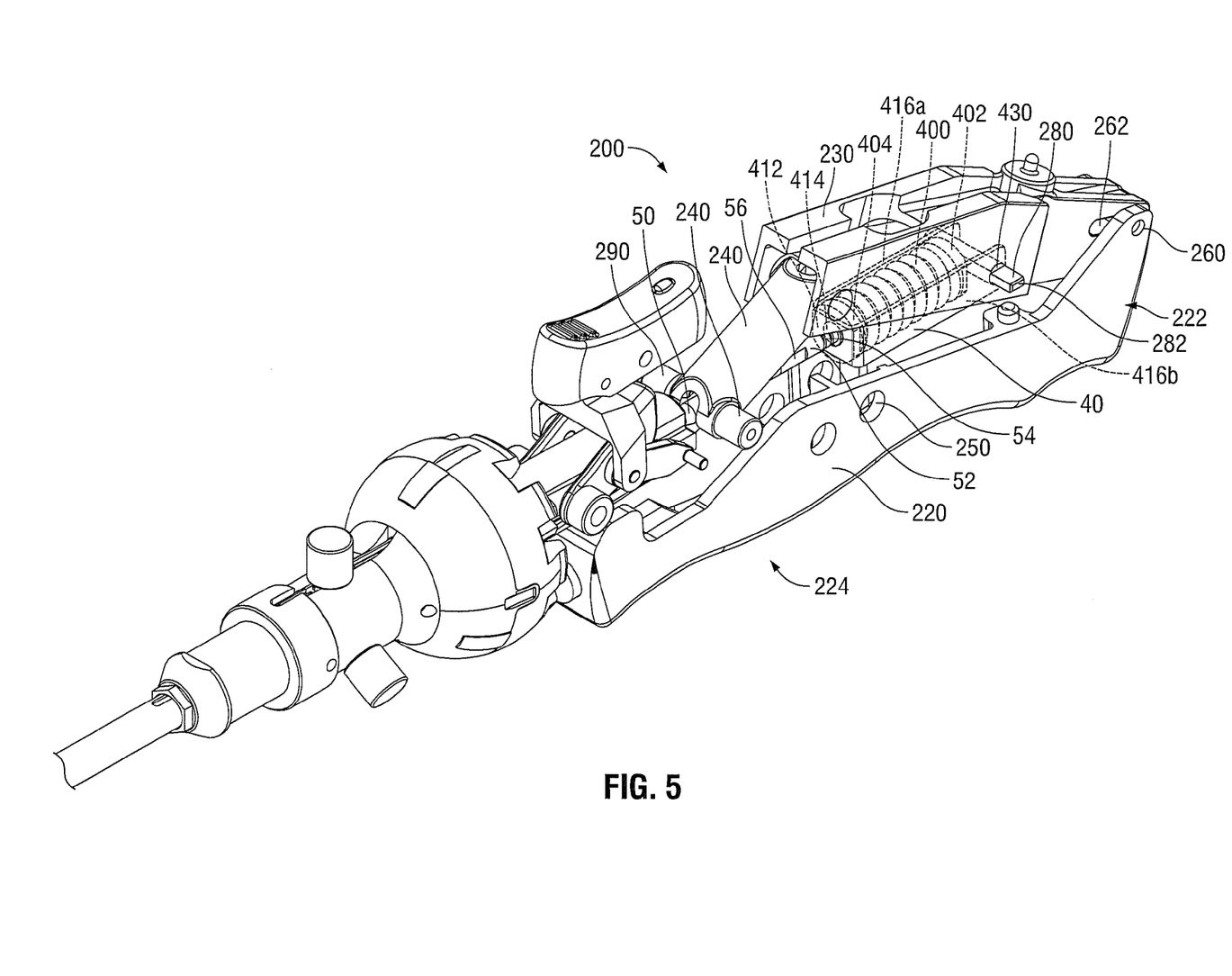
FIG. 5 is a perspective view of the handle assembly of the present disclosure with portions of the housing omitted.

With reference to FIG. 5, a proximal portion 52 of tip catheter 50 includes a plurality of grooves 54 formed within proximal portion 52 and a "C"-clip to help fix the position of a spring member 400 (other types of fasteners other than "C"-clips are also envisioned and within the scope of the present disclosure). Spring member 400 is disposed coaxially with the catheter tip 50 adjacent the proximal portion 52 of the tip catheter 50. A proximal end 402 of the spring member 400 is in contact with the "C"-clip, and a distal end 404 of the spring member 400 contacts a yoke 410. (It is envisioned that a nut/bushing assembly could be used in lieu of the grooves 54 and "C"-clip.) The yoke 410 is generally U-shaped, with the base 412 being distally disposed and including a through hole 414 to enable longitudinal translation of the tip catheter 50 therethrough. Yoke 410 also includes side walls 416a, 416b, which help constrain the spring member 400, and the "C"-clip. Further, yoke 410 is sized such that the distance between side walls 416a, 416b prevents rotation of the "C"-clip. Yoke 410 also includes a second through hole 430 (e.g., a "D"-shaped hole), which is disposed transverse to the longitudinal axis A-A, extends through both side walls 416a, 416b, and allows a fourth pivot member 280 to pass therethrough. The second through hole 430 and/or the transverse cross-section of fourth pivot member 280 may be "D"-shaped to prevent rotation of the fourth pivot member 280 about its axis. The fourth pivot member 280 may also include a bore therethrough to allow longitudinal translation of the tip catheter 50 therethrough. Additionally, through hole 430 may be disposed half way (or substantially half way) along the length of proximal link 230.

In the illustrated embodiment, ends 282 of fourth pivot member 280 include flat surfaces, which mate within molded longitudinal guide tracks in the sides of the housing 20. This assembly is designed to enable the yoke 410/fourth pivot member 280 to longitudinally translate within the handle housing 20. Additionally, the tip catheter 50 includes a groove 56 for receiving a retaining ring, and thus providing a stop feature to facilitate assembly, for instance. Accordingly, the tip catheter 50 is able to proximally translate within the housing 20 without necessarily effecting the length of the spring member 400 (e.g., without compressing spring member 400). More particularly, the length of the spring 400 may be effected (e.g., if "backlash" is desired) depending on whether the spring 400 is preloaded and/or the location of the groove 54 engaged by the "C"-clip. As discussed in further detail below, actuation of proximal portion 222 of movable handle 220 causes tip catheter 50 to move proximally to approximate the jaw members. After the jaw members have contacted each other, additional proximal movement of fourth pivot member 280 (e.g. "over travel") causes yoke 410 to move proximally, thus compressing the spring member 400 and resulting in a load being applied to the tissue-contacting surfaces of the jaw members. The amount of load is determined by the amount of "over travel," and the spring constant, and can be selected by the manufacturer for various purposes.

With continued reference to FIGS. 5-8, a detailed description of actuation of handle assembly 200 is described herein. As discussed above, longitudinal translation (both proximal and distal translation) of tip catheter 50 is caused by actuation of movable handle 220. More particularly, a proximal portion 222 of movable handle 220 is pivotably attached to a proximal portion 232 of proximal link 230 via a second pin 260 and a through slot 262. A distal portion 234 of proximal link 230 is pivotably connected to a proximal portion 242 of distal link 240 via a third pivot 270. A distal portion 244 of distal link 240 is disposed in mechanical cooperation with the handle housing 20 via a pair of pins 290, with each pin 290 being disposed on a lateral side of the tip catheter 50 (see FIG. 5).

Figure 7:
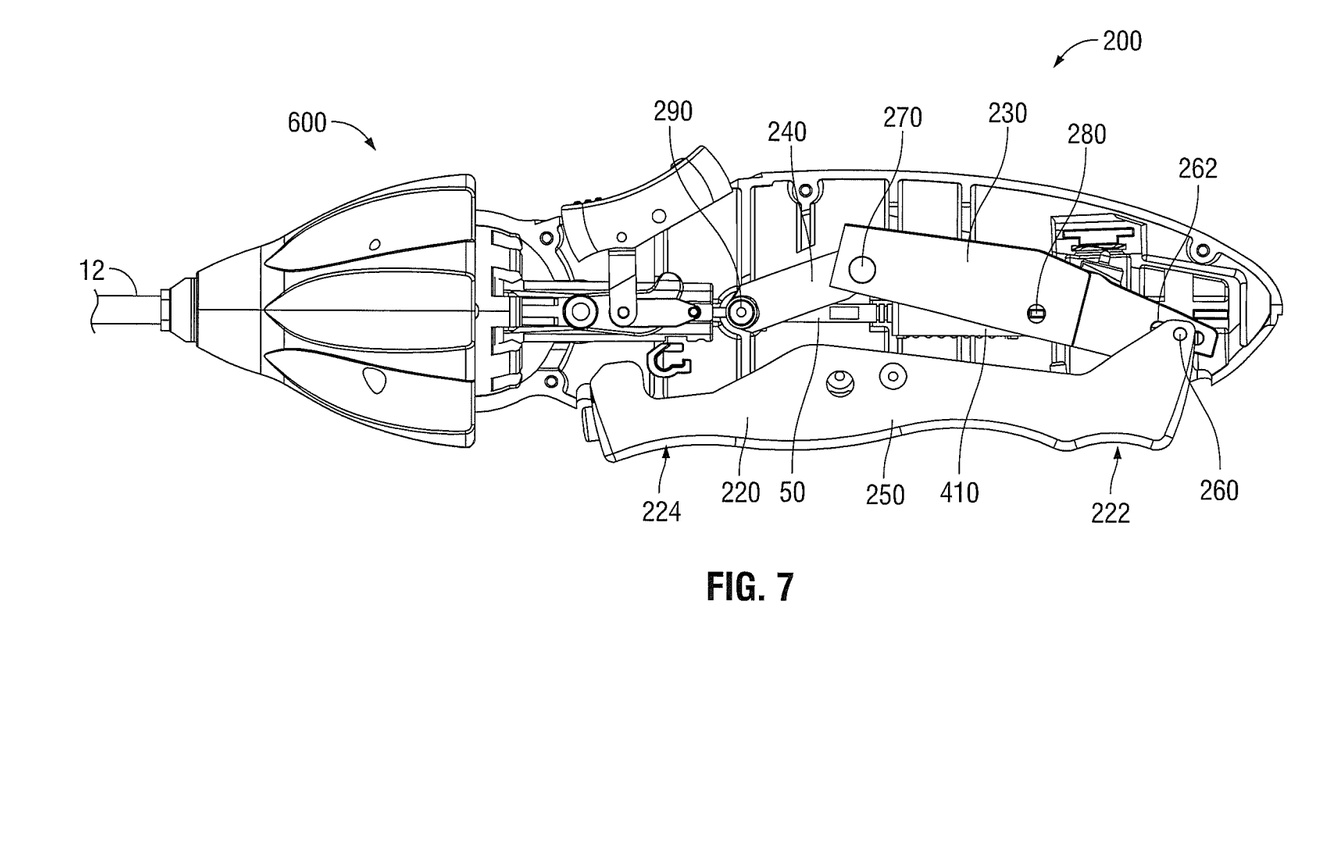
Figure 8:
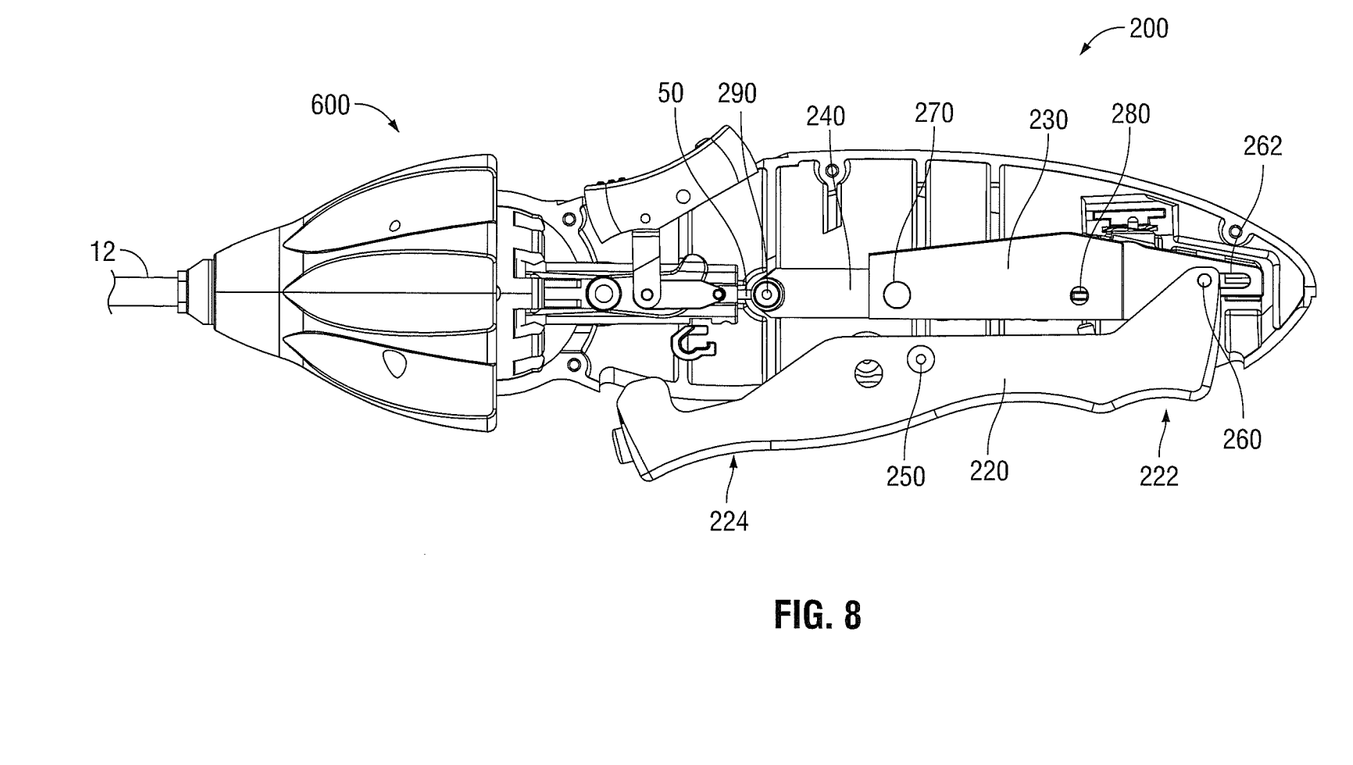

Accordingly, actuation of proximal portion 222 of movable handle 220 causes second pin 260 to move distally within through slot 262, which causes third pivot 270 to move toward the longitudinal axis A-A, thus causing proximal translation of fourth pivot member 280, yoke 410 and tip catheter 20, which approximates the jaw members (see FIG. 8). Actuation of distal portion 224 of movable handle 220 causes second pin 260 to move proximally within through slot 262, which causes third pivot 270 to move away from the longitudinal axis A-A, thus causing distal translation of fourth pivot member 280, yoke 410 and tip catheter 20, which opens the jaw members (see FIG. 6). FIG. 7 illustrates movable handle 220 between its first position, where the jaw members in an open position (FIG. 6), and its second position, wherein the jaw members are approximated (FIG. 8).

It is further envisioned that pivots 250, 270, 280 and/or second pin 260 can be positioned in different locations (e.g., farther proximally or farther distally) to alter the mechanical effects related to actuation of different portions (e.g., proximal portion 222 or distal portion 224) movable handle 200, for example.

While several embodiments of the disclosure have been depicted in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising;
a handle assembly including a housing and a movable handle that is configured to be engaged by a user;
an elongated shaft extending distally from the handle assembly and defining a first longitudinal axis;
an end effector disposed in mechanical cooperation with a distal portion of the elongated shaft, the end effector defining a second longitudinal axis, the end effector includes jaw members that are movable between an open position and an approximated position; and
an actuation rod disposed in mechanical cooperation with the handle assembly and with the end effector, the actuation rod configured for longitudinal translation with respect to the handle portion;
wherein the movable handle is movable between a first position where the jaw members of the end effector are in an open position and a second position where the jaw members are in an approximated position, wherein the movable handle is disposed substantially parallel to the first longitudinal axis when the movable handle is in one of the first position, the second position or any position therebetween, wherein at least a majority of the movable handle is disposed on a first side of the first longitudinal axis when the movable handle is in one of the first position, the second position or any position therebetween, a proximal portion of the movable handle is pivotally attached to a proximal portion of a proximal link, a distal portion of the proximal link is pivotally attached to a proximal portion of a distal link via a first pin, the first pin being movable towards and away from the first longitudinal axis, wherein the first pin is disposed on a second side of the first longitudinal axis when the movable handle is in the first position, and a distal portion of the distal link being pivotably connected to the housing via a second pin.

2. The surgical instrument of claim 1, wherein the movable handle is pivotable about a fulcrum that is disposed between the proximal portion of the movable handle and a distal portion of the movable handle, wherein pivoting the proximal portion of the movable handle causes the actuation rod to move in a first longitudinal direction, and wherein pivoting the distal portion of the movable handle causes the actuation rod to move in a second longitudinal direction, the first longitudinal direction being opposite from the second longitudinal direction.

3. The surgical instrument of claim 2, wherein the fulcrum is disposed substantially in the longitudinal center of the movable handle.

4. The surgical instrument of claim 1, wherein the second pin is aligned with the first longitudinal axis.

5. The surgical instrument of claim 1, further comprising a rotation mechanism disposed in mechanical cooperation with the handle assembly for effecting rotation of the end effector about the second longitudinal axis, the rotation mechanism including a first member including at least one magnet disposed in mechanical cooperation therewith, and a second member including at least one magnet disposed in mechanical cooperation therewith, the first member and the second member defining a space therebetween.

6. The surgical instrument of claim 5, further comprising an articulation mechanism disposed in mechanical cooperation with the handle assembly for effecting movement of the end effector from a first position where the first longitudinal axis is substantially aligned with the second longitudinal axis to a second position where the second longitudinal axis is displaced from the first longitudinal axis, the articulation mechanism including a plurality of tendons, each tendon extending longitudinally through the space between the first member and the second member of the rotation mechanism.

7. The surgical instrument of claim 6, wherein each tendon is configured to maintain its radial position in response to actuation of the rotation mechanism to rotate the end effector about the second longitudinal axis.

8. The surgical instrument of claim 1, wherein a portion of the proximal link is disposed in mechanical cooperation with the actuation rod.

9. The surgical instrument of claim 1, wherein the first pin is always disposed on a second side of the first longitudinal axis when the movable handle is in the first position.

10. The surgical instrument of claim 1, wherein the second pin is always aligned with the first longitudinal axis.

* * * * *